United States Patent [19]
Knoderer

[11] Patent Number: 4,727,867
[45] Date of Patent: Mar. 1, 1988

[54] MANDIBULAR LATERAL MOTION INHIBITOR

[76] Inventor: William R. Knoderer, 4613 Stonewall, Greenville, Tex. 75401

[21] Appl. No.: 832,472

[22] Filed: Feb. 24, 1986

[51] Int. Cl.⁴ .............................................. A61F 5/46
[52] U.S. Cl. .................................................. 128/136
[58] Field of Search ................ 128/136, 137, 325, 12; 433/167, 215, 229, 6, 5

[56] References Cited

U.S. PATENT DOCUMENTS

| | | | |
|---|---|---|---|
| 2,037,079 | 11/1934 | Locke | 128/136 |
| 2,077,245 | 9/1936 | Locke | 128/136 |
| 3,132,647 | 5/1964 | Corniello | 128/136 |
| 3,224,442 | 12/1965 | Stubbs | 128/136 |
| 3,307,539 | 3/1967 | Peterson | 128/136 |
| 4,273,530 | 6/1981 | Broussard | 433/6 |
| 4,457,708 | 7/1984 | Dofour | 433/6 |
| 4,471,771 | 9/1984 | Steven et al. | 128/136 |

Primary Examiner—Robert Peshock
Attorney, Agent, or Firm—Dennis T. Griggs

[57] ABSTRACT

A dental appliance for controlling the weight of an individual by slowing down the rate of food ingestion to allow the body time to naturally register the sensation of being full is disclosed. The appliance includes a metal frame having a curved front portion and opposed arms extending rearwardly with first and second wing members mounted thereon. The wing members are contoured to conform to the shape of the lower jaw between the teeth and tongue. The lower jaw is constrained for vertical movement only with lateral movement being opposed by its engagement with the facing surface of a wing member. When the appliance is positioned within the user's oral cavity, lateral movement of the lower jaw with respect to the upper jaw is inhibited while normal up-and-down biting movement is permitted. The chewing process is slowed down and the rate of food ingestion is reduced because grinding action is prevented.

17 Claims, 15 Drawing Figures

MANDIBULAR LATERAL MOTION INHIBITOR

FIELD OF THE INVENTION

The present invention relates generally to weight control devices, and in particular to a prosthodontic appliance for limiting lateral motion of the mandible.

BACKGROUND OF THE INVENTION

Weight control is a problem faced by many people, particularly in the United States where food is abundant. Foods high in animal fat, such as red meat, and high in carbohydrate content, such as sugars and starches, are avoided or consumed in moderate amounts by one who is seeking to lose or control his weight. Special diets are often prescribed for such persons.

Typically, there is a time lag between the entry of food into the digestive track and the assimilation of nutrients into the blood stream. As much as twenty minutes may be required from the time that food reaches the stomach lining for it to be digested and absorbed into the blood stream. In response to absorption of nutrients into the blood stream, a message of nourishment is transmitted to the hunger center of the brain, which triggers a sensation of being full. Accordingly, the rapid ingestion of foods until the hunger sensation is satisfied will invariably lead to excessive food intake because of the inherent time lag. In view of the foregoing it is generally recommended that solid foods be chewed thoroughly so that the digestive process can be accelerated in addition to slowing down the actual rate of food consumption. Generally, the smaller the particles of food that are taken into the digestive tract the more rapid is the assimilation of nutrients into the blood stream, which results in a feeling of satisfaction with less food intake.

DESCRIPTION OF THE PRIOR ART

Among the various methods of weight control, the most common method is a diet in which the individual voluntarily limits the type and quantity of food eaten. In many cases a liquid diet is prescribed, particularly when one desires to lose weight rapidly. One method of encouraging an individual to adhere to a liquid diet is to prevent him from opening his mouth wide enough to take in solid foods. This method, in which the jaws are fastened together in closed relation (jaws wired shut), is effective but is unsafe because of the risk of choking, and produces undesirable side effects, such as impairment of speech, unsightly appearance and the difficulty in maintaining proper oral hygiene.

Other methods of weight control involve the placement of appliances inside the oral cavity. One such device uses a sieve disposed in the back of the mouth to allow finely particulated food and liquids to pass through the sieve, but to block large solid foot particles from entering the esophagus. Another type of device is positioned between the outside surfaces of the lower teeth and cheeks of the individual, so as to stimulate the flow of saliva and thereby reduce the individual's desire for food. Such prior art devices may interfere with regurgitation, are typically uncomfortable and unsightly. The need therefore exists for an effective weight control appliance which can be fitted within the oral cavity of an individual and which can be worn comfortably and safely without detracting from the user's appearance.

OBJECTS OF THE INVENTION

It is, therefore, the principal object of the present invention to provide an improved weight control device.

Another object of the invention is to provide a prosthodontic appliance which is operable within the oral cavity of an individual to slow down the rate at which food is ingested.

Still another object of the invention is to provide an appliance which can be comfortably and conveniently worn inside the oral cavity of a user for weight control purposes.

A related object of the invention is to provide a prosthodontic appliance to reduce the rate of mastication of food.

SUMMARY OF THE INVENTION

The foregoing objects are accomplished in accordance with the present invention wherein a prosthodontic appliance is provided for slowing down the rate of food ingestion to allow the body time to naturally register the sensation of being full. I have discovered that the rate at which food is chewed and ingested can be substantially reduced by inhibiting lateral movement of the mandible. Normal chewing movements involve lateral as well as vertical displacement of the mandible. The resultant oscillatory movement produces a grinding effect. By inhibiting lateral movement, only a "chopping" effect is produced as the lower jaw moves up and down.

Mandibular lateral motion is inhibited, according to the present invention, by an appliance having a frame member with a curved front portion and opposed arms extending rearwardly from the front portion; first and second wing members disposed on respective opposed arms of the frame member; and means for securing the appliance in a predetermined position within the oral cavity between the teeth and tongue so that the first and second wing members will extend vertically between respective first positions adjacent to the user's bottom teeth and respective second positions adjacent to the user's top teeth on opposite sides of the mouth, to inhibit lateral movement of the lower jaw with respect to the upper jar during mastication, thereby slowing down the eating process and reducing the gross quantity of food ingested.

In one embodiment each of the first and second wing members has first and second oppositely positioned, relatively flat faces. The first face is disposed in facing relationship with selected bottom teeth and adjacent thereto and the second face is positioned in facing relationship with the tongue when the device is secured within the lower oral cavity. The frame member further includes a plurality of rest members projecting substantially laterally outward for engaging the top surfaces of selected bottom teeth to stabilize the device within the oral cavity. The rest members are integrally formed at selected positions on the opposed arms of the frame member so that each rest member will engage an occlusal surface of an appropriate tooth, as selected by the dentist.

The tongue facing surface of each wing member is preferably smooth with a narrow groove formed therein and a pair of openings positioned at respective opposite ends thereof. The openings communicate between the opposite faces for receiving respective ends of a wire for anchoring the device in a predetermined position within the oral cavity by wrapping the ends of the wire around a selected tooth on each side of the mouth and securing the ends on the cheek side of the tooth.

BRIEF DESCRIPTION OF THE DRAWINGS

Other objects and advantages of the invention will be apparent from the detailed description and claims when read in conjunction with the accompanying drawings wherein:

DETAILED DESCRIPTION OF THE PREFERRED EMBODIMENT

Figure 1:
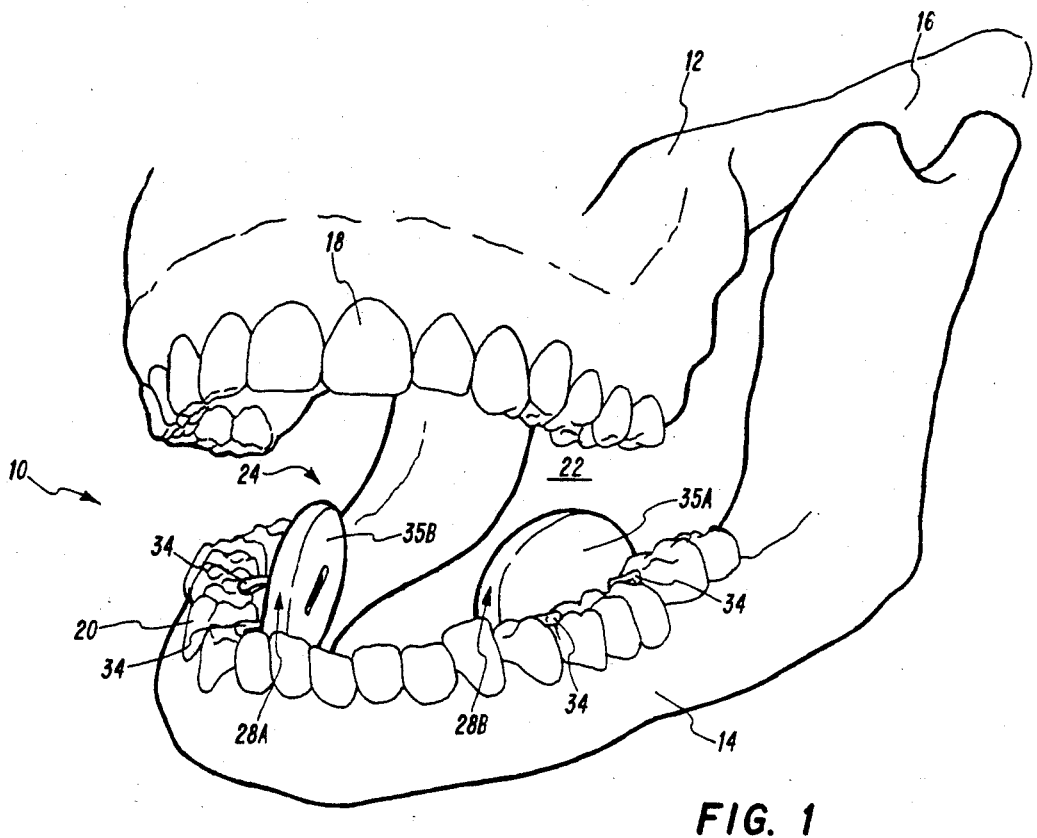
FIG. 1 is a simplified frontal perspective view of upper and lower jaw bone structures having a lateral motion inhibitor appliance fitted onto the teeth of the lower jaw.

In the description which follows, like parts are marked throughout the specification and drawings with the same reference numerals, respectively. The drawings are not necessarily to scale and in some instances proportions have been exaggerated in order to more clearly depict certain features of the invention.

Referring to FIG. 1, a human jaw structure 10 is depicted. The jaw structure 10 is comprised of upper (maxillary) jaw 12 and lower (mandibular) jaw 14, which is hingedly connected by muscle tissue at joint 16 with respect to upper jaw 12 for three dimensional movement with respect thereto. Joint 16 in effect forms a gimbal to allow lower jaw 14 to move vertically and laterally with respect to upper jaw 12. Upper jaw 12 and lower jaw 14 include top teeth 18 and bottom teeth 20, respectively. Disposed within oral cavity 22 on the tongue side of bottom teeth 20 and adjacent thereto is a mandibular appliance 24 according to the present invention, for inhibiting the lateral motion of the lower jaw with respect to the upper jaw during mastication.

Referring to FIGS. 3A, 3B, 3C and 3D, appliance 24 includes an arched metal frame member 26 which conforms with the contours of the gumline beneath bottom teeth 20 on the tongue side thereof, and a pair of wing members 28A, 28B formed on opposed arms 26A and 26B, respectively, of frame member 26. Frame member 26 also has four rest members 34 for engaging the top of selected bottom teeth 20 to stabilize device 24 inside oral cavity 22. Rest members 34 are preferably formed in pairs on frame member 26 so that each rest member 34 extends outwardly from arms 26A, 26B.

Frame member 26 is preferably comprised of cast chromium cobalt nickel-based alloy material and is manufactured in accordance with standard lost wax casting techniques as commonly performed in dental laboratories. Frame member 26 is manufactured to conform to the shape of the patient's lower jaw 14 by casting frame member 26 in place within a stone model of lower jaw 14. The stone model is formed in the conventional manner by taking an alginate impression of the patient's lower jaw 14 and bottom teeth 20 and upper jaw 12 and top teeth 18. The alginate impression is filled and allowed to harden, which yields a stone replica of the patient's teeth and jaw structure. By casting metal frame member 26 in place within the stone replica, appliance 24 is custom fitted for each patient.

After frame member 26 is formed, wing members 28A, 28B are manufactured by applying an orthodontic acrylic material, preferably containing the ingredient methylmethacrylate polymer, along opposed arms 26A, 26B of frame member 26. The acrylic material, which is initially in the form of a powder, is mixed with methylmethacrylate monomer to form a paste and is then brushed onto arms 26A and 26B. The material is manually shaped with the aid of the stone replica to conform with the adjoining mandibular and maxillary surfaces. Once the acrylic material has hardened, an acrylic burr tool is used to smooth and refine the shapes of the surfaces of wing members 28A, 28B. The wing members are curved slightly in both the longitudinal and transverse directions to eliminate sharp edges. Each wing member 28A, 28B has relatively flat major surfaces 35A and 35B on opposite sides thereof in facing relationship between bottom teeth 20 and the patient's tongue, respectively.

Figure 2:
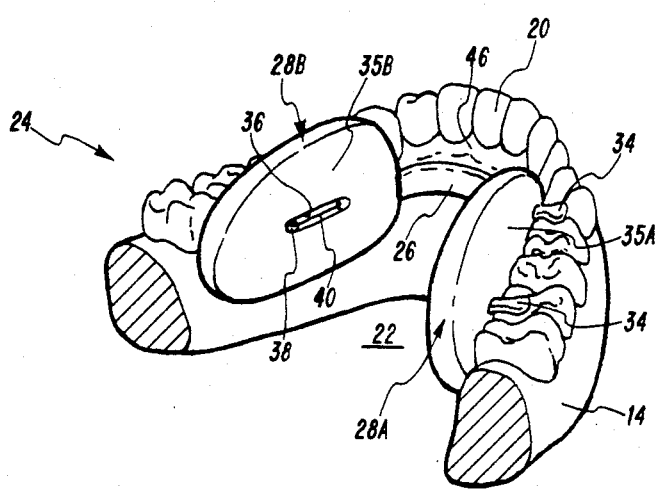
FIG. 2 is a perspective view partly broken away, of the lower teeth and jaw, showing the mandibular embodiment disposed within the oral cavity.
Figure 3A:
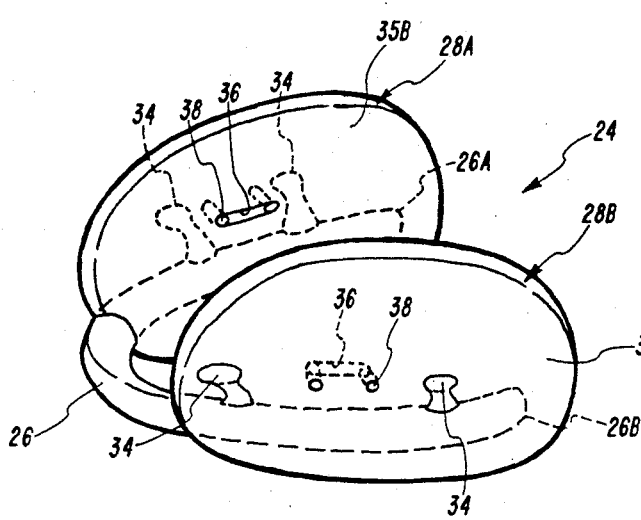
FIGS. 3A, 3B, 3C and 3D are side perspective, left side elevation, front elevation and top perspective views, respectively, of the mandibular embodiment.
Figure 3B:
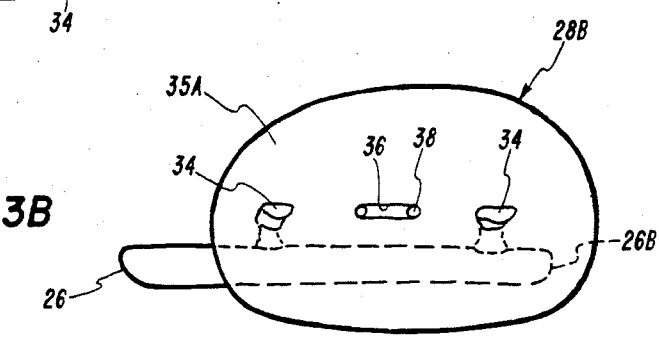
Figure 3C:
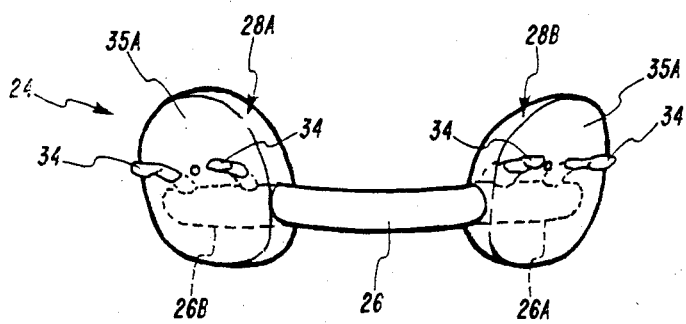
Figure 3D:
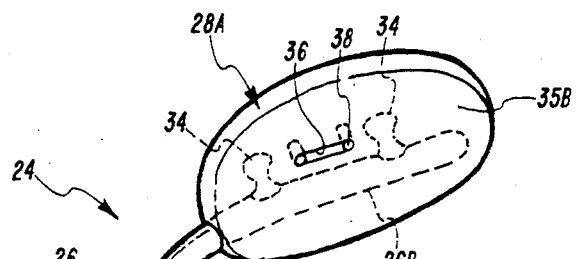
Figure 3D:
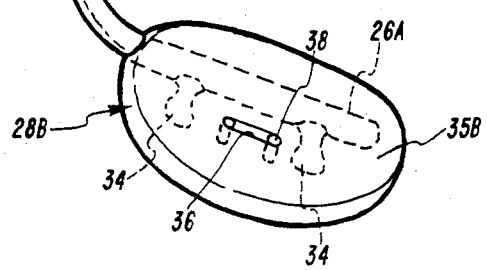
Figure 4:
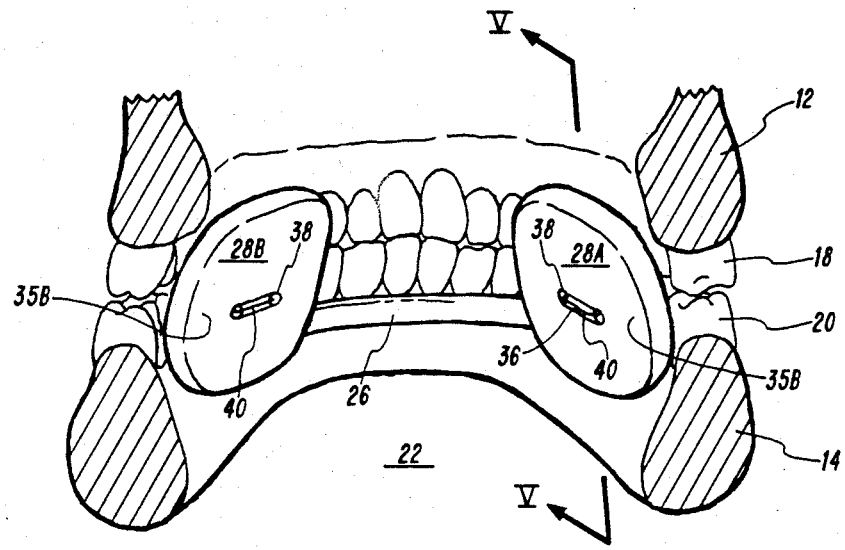
FIG. 4 is a rear elevation view from inside the oral cavity of the mandibular embodiment.
Figure 5:
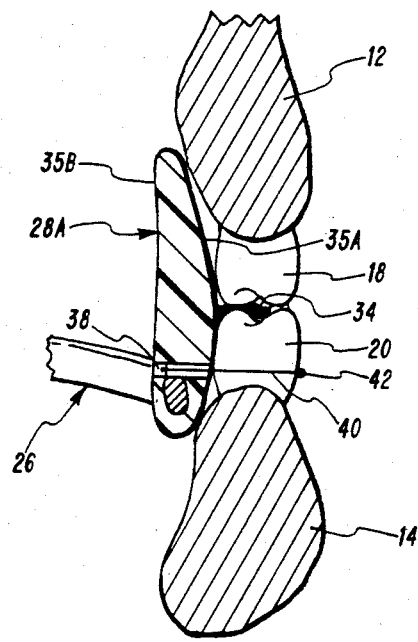
FIG. 5 is a sectional view of the mandibular embodiment taken along the line V—V in FIG. 4.
Figure 6:
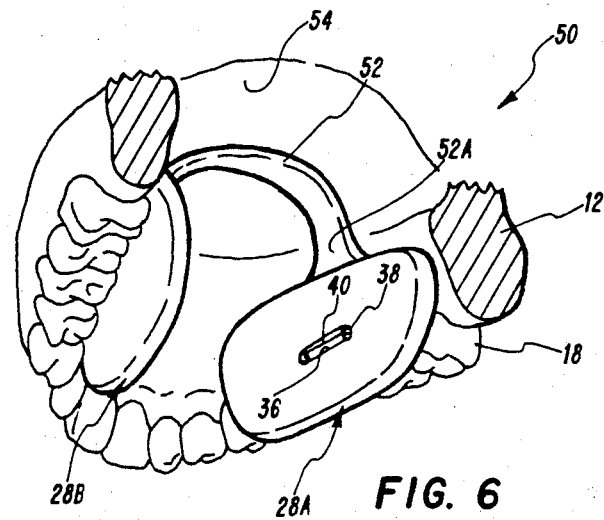
FIG. 6 is a bottom plan view of a maxillary embodiment of the invention in which a lateral motion inhibitor is attached to the teeth of the upper jaw.
Figure 7A:
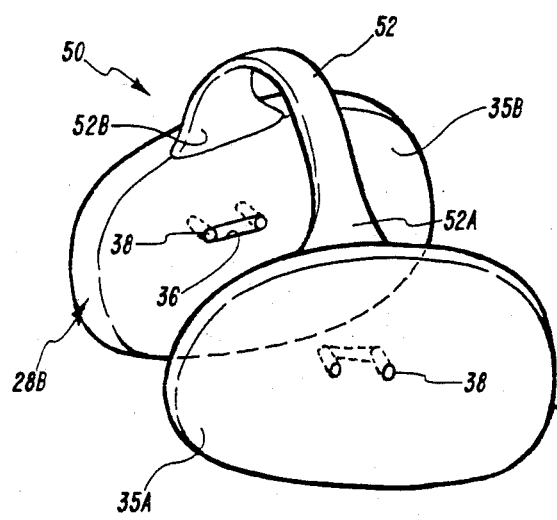
FIGS. 7A, 7B, 7C and 7D are side perspective, left side elevation, front elevation, and top perspective views, respectively, of the maxillary embodiment of the invention.
Figure 7B:
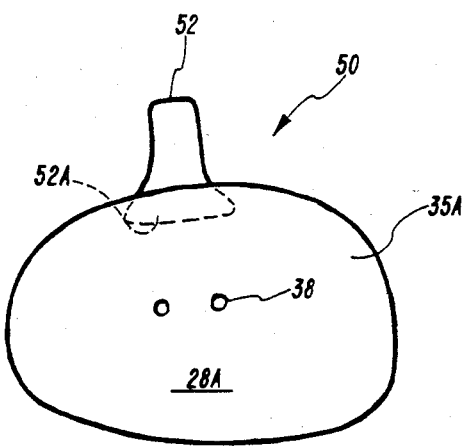
Figure 7C:
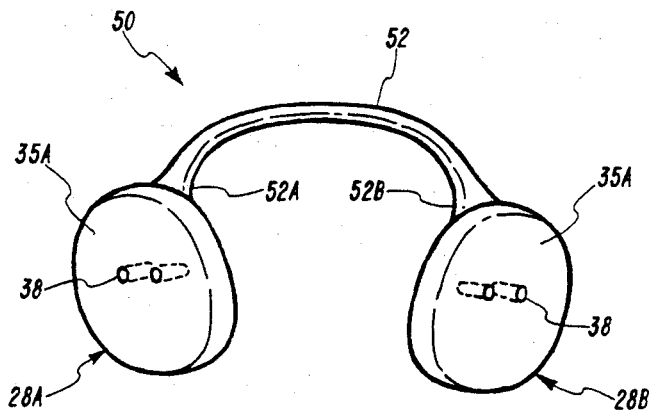
Figure 7D:
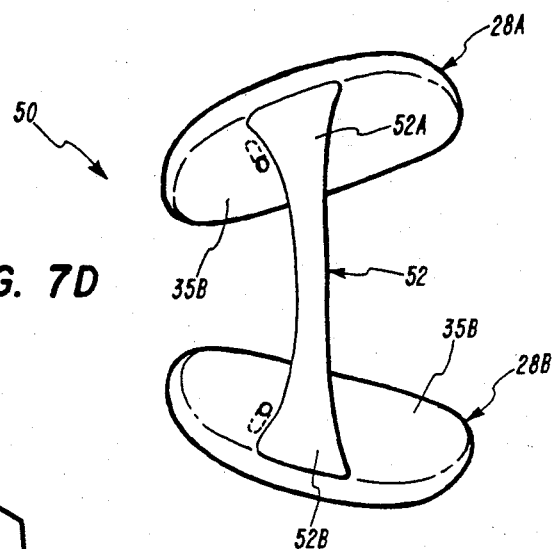
Figure 8:
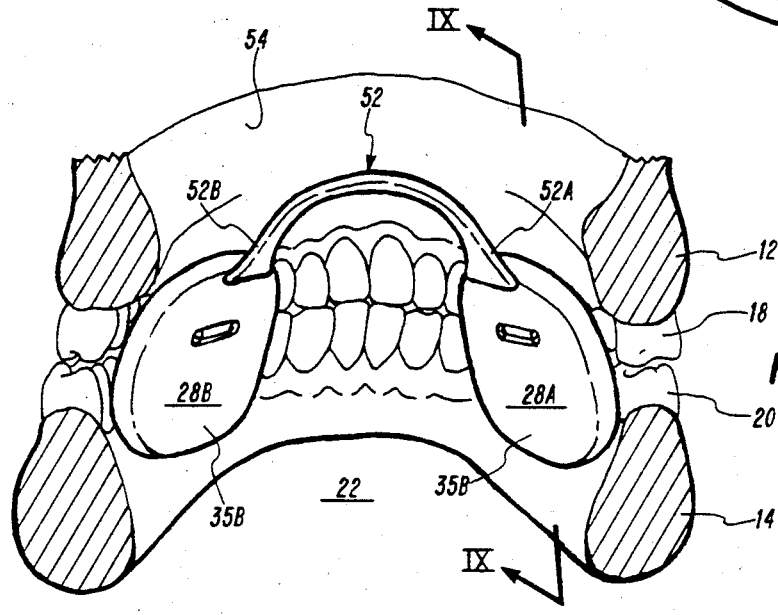
FIG. 8 is a rear elevation view of the maxillary embodiment from inside the oral cavity; and, FIG. 9 is a sectional view of the maxillary embodiment taken along the line IX—IX of FIG. 8.
Figure 9:
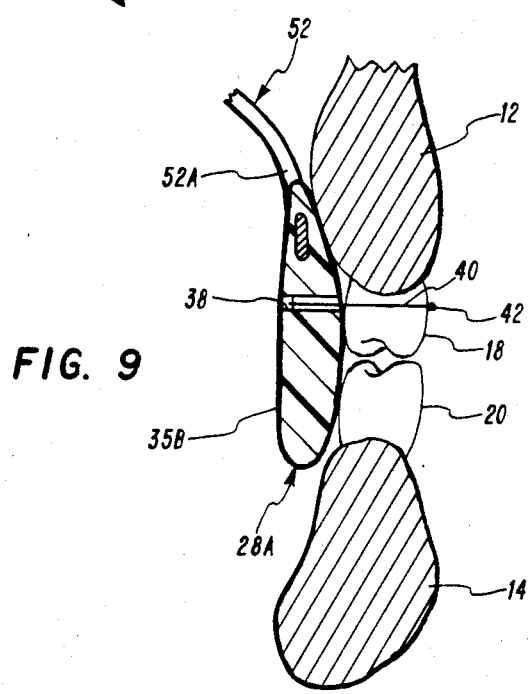

Referring to FIGS. 2, 4 and 5, each wing member 28A, 28B includes an elongated slot 36 formed in major surface 35B slightly below the geometric center thereof. Each slot 36 includes a pair of openings 38 disposed at opposite ends of the corresponding slot 36. A wire 40 secures appliance 24 in place within oral cavity 22. Opposed ends of wire 40 are threaded through corresponding holes 38 on opposite ends of each slot 36 and wrapped around a selected bottom tooth 20 on each side of lower jaw 14. The ends of wire 40 are then tied together on the cheek side of the selected bottom tooth 20, as inciated generally at 42 and the free ends are tucked into the respective spacings between the particular bottom tooth 20 and adjacent teeth 20 on each side of the particular tooth 20. The portion of wire 40 which extends between openings 38 is received within slot 36 on the tongue side. Wire 40 is preferably 0.016 inch stainless steel ligature wire.

One skilled in the art will appreciate that lateral motion inhibitor appliance 24 described above must be custom fitted to precise dimensions in accordance with the size and shape of each patient's oral cavity for optimum effectiveness. For example, it has been determined that a clearance of 1-3 mm should be allowed between the curved portion 44 of frame member 26 and the adjacent gumline 46 below bottom teeth 20 at the front of the patient's mouth, as illustrated in FIG. 2. Each wing member 28 should have a thickness of approximately 2 to 3 mm and a length of approximately 25-35 mm so that each wing member extends from the distal of the first bicuspid to the region of the second molar.

Mandibular appliance 24 is positioned within oral cavity 22 so that each wing member 28A, 28B is in contact with only one bottom tooth 20 (on each side) and has a clearance of approximately 1 mm between major surface 38A and the remaining bottom teeth 20. The corresponding slot 36 is approximately centered with respect to the selected bottom tooth 20, which is in contact with the corresponding wing member 28, so that the ends of wire 40 can be wrapped around the selected tooth 20, for anchoring appliance 24 as described above. When appliance 24 is properly positioned within oral cavity 22, each rest member 34 engages the occlusal surface of a single tooth or adjacent occlusal surfaces of a corresponding pair of adjacent bottom teeth 20 so as to span the gap between the teeth, as shown in FIGS. 1 and 2.

Each wing member 28 preferably extends vertically 4 to 15 mm above the tooth line of bottom teeth 20 so that when the patient's mouth is closed and top and bottom teeth 18 and 20 are in contact, each wing member 28A, 28B extends upwardly to approximately the level of the gumline of top teeth 18. During mastication, lower jaw 14 tends to move laterally as well as up and down with respect to upper jaw 12 to create a grinding action on the food being chewed. Surfaces 35A of appliance 24 oppose lateral movement of lower jaw 14 by contacting top teeth 18. Thus, wing members 28A, 28B serve as mechanical stops to limit lateral movement of lower jaw 14 in either direction. The lower jaw is accordingly permitted only up-and-down "chopping" movement which prevents the grinding action of the teeth and results in slower mastication of food.

A further reduction in the rate of ingestion of food is brought about by the shielding effect of the wing members 28A, 28B. That is, each shield member in combination with the teeth and adjacent cheek defines a pocket which retains food as it is being chewed. In the absence of the wing members 28A, 28B food is easily transferred by the tongue and by swallowing movements from the chewing region into the oral cavity. However, because of the presence of the wing members 28A, 28B the pattern of normal movement of food within the mouth is interrupted, with the chewed food tending to remain in the pocket between the shield and the cheek. Extra effort is required to transfer the food from the pocket so that it can be swallowed. The shielding effect prolongs the chewing process which further reduces the rate at which food is ingested.

Because the patient must chew his food more slowly, he is able to ingest less food in a given time period. As a result, the food reaching the stomach can be digested and absorbed into the blood stream to cause the brain to generate a "full" signal before an excessive amount of food is ingested.

The appliance according to the present invention can be comfortably and safely worn by an individual without detracting from his appearance. However, the user will consume substantially reduced quantities of food while achieving the same degree of hunger satisfaction as before.

The weight control appliance according to the present invention may be embodied in a maxillary arrangement 50 as illustrated in FIGS. 6, 7A, 7B, 7C, 7D, 8 and 9. In the maxillary arrangement 50, frame member 52 conforms with the palate and is secured to selected top teeth 18 in lieu of bottom teeth 20 as described above. Frame member 52 is molded according to the same procedure as frame 26, but extends transversely across and in conformed engagement with the palate 54. Frame 52 is provided with depending arm portions 52A, 52B onto which rests 34 are formed. Wing members 28A, 28B are attached to the arm portions 52A, 52B respectively, in the same manner as the mandibular embodiment. When maxillary appliance 50 is positioned in the upper oral cavity 22, surfaces 35A on the tooth side of wing members 28A, 28B will serve as mechanical stops to contact bottom teeth 20 and inhibit lateral movement of lower jaw 14 with respect to upper jaw 12.

Two preferred embodiments of the invention have been described in detail. Since changes in and modifications to the above-described preferred embodiments may be made without departing from the nature, spirit and scope of the invention, the invention is not to be limited to said details, except as set forth in the appended claims.

What is claimed is:

1. An appliance for inhibiting lateral movement of the lower jaw with respect to the upper jaw in a person's mouth, said appliance comprising, in combination:
    a frame member;
    a wing member disposed on said frame member; and,
    means for securing said frame member onto a selected lower or upper tooth with the appliance being held within the oral cavity in a predetermined position between the person's teeth and tongue, said wing member extending vertically between a first position adjacent to the bottom teeth and a second position adjacent to the top teeth, whereby lateral movement of the lower jaw is opposed by engagement of one of the upper or lower teeth against said wing member.

2. An appliance as defined in claim 1 wherein said frame member is shaped to approximate the contour of the lower jaw between the teeth and tongue, with said frame member being attachable to a lower tooth.

3. An appliance as defined in claim 1 wherein said frame member is shaped to approximate the contour of the palate, with said frame member being attachable to an upper tooth.

4. An appliance as defined in claim 1 wherein said wing member has first and second oppositely positioned, relatively flat faces, said first face being positioned for facing relationship with selected teeth and adjacent thereto, said second face being positioned for facing relationship with the person's tongue.

5. An appliance as defined in claim 4 wherein said second flat face of each of said wing member has a slot formed therein and a pair of openings positioned at respective opposite ends of the slot, said openings communicating between the first and second flat faces for receiving respective ends of a wire to enable the appliance to be secured in a predetermined position within the mouth by wrapping the ends of the wire around a selected tooth on each side of the mouth and securing the ends on the cheek side of the tooth.

6. An appliance as defined in claim 5 wherein said slot is aligned with said selected tooth on the corresponding side of the user's mouth so that said openings are substantially aligned with spaces between said selected tooth and adjacent teeth on either side thereof, to enable the respective ends of the wire to be wrapped around said selected tooth.

7. An appliance as defined in claim 1 wherein said frame member comprises a metal alloy cast material.

8. An appliance as defined in claim 1, wherein said wing member comprises an acrylic material.

9. An appliance as defined in claim 1, said frame member being conformed with the corresponding front portion of the person's lower jaw between the teeth and tongue and having a predetermined spacing between said frame member and the adjacent gumline of the person's lower jaw when said appliance is mounted onto the person's lower teeth.

10. An appliance as defined in claim 1, wherein said frame member inlcudes a plurality of rest members extending substantially laterally outward therefrom for engaging the occlusal surface of a selected tooth to stabilize the appliance within the person's mouth.

11. An appliance as defined in claim 10, said frame member including first and second arms, wherein said rest members are integrally formed at selected positions on said first and second arms.

12. An appliance as defined in claim 10 wherein each of said rest members is located on said frame member so that each projection member will engage the occlusal surfaces of two adjacent teeth and will span the gap therebetween to stabilize the appliance within the person's mouth.

13. A weight control appliance mountable onto teeth within an oral cavity for slowing down the rate of food consumption, said appliance comprising, in combination:
   a frame member having opposed arms;
   first and second wing members disposed on respective opposed arms of said frame member, each of said wing members having first and second oppositely positioned relatively flat faces, the respective major axes of which extend longitudinally along the corresponding arm and the respective minor axes of which extend vertically with respect to the corresponding arm, said first flat face for being disposed in facing relationship with selected teeth and adjacent thereto and said second flat face for being disposed in facing relationship with the user's tongue;
   a plurality of projection members extending laterally outward from said frame member for engaging the biting surfaces of selected teeth to stabilize the device within the oral cavity;
   each of said second flat faces having a slot formed therein and a pair of openings positioned at opposite ends of said slot, said openings communicating between said first and second flat faces for receiving respective ends of a wire for securing the appliance within the user's oral cavity by wrapping the ends of the wire around a particular one of the user's teeth and securing the ends thereof together on the cheek side of the tooth; and,
   said first and second wing members being configured to extend vertically between the user's top and bottom teeth to inhibit lateral movement of the lower jaw with respect to the upper jaw during mastication.

14. The device according to claim 13 wherein said frame member is shaped to approximate the contour of the user's lower jaw between the teeth and the gums and the first flat face of each of the first and second members is contoured to approximate the contour of the corresponding portion of the user's lower teeth and jaw which is adjacent to the corresponding first flat face.

15. A method for controlling the weight of an individual by slowing down the rate of food consumption, said method comprising:
   inhibiting lateral movement of the lower jaw relative to the upper jaw with a blocking member having a facing portion receiving within the oral cavity intermediate the tongue and jaws, said facing portion overlapping at least one upper and one lower tooth when the upper and lower jaws are closed, wherein lateral movement of the lower jaw is opposed by engagement of one of said teeth against the blocking member while permitting normal up-and-down jaw movement.

16. A method for controlling the weight of an individual in which the rate of food ingestion is reduced, said method comprising:
   interposing a mechanical shield within the oral cavity intermediate the tongue and lower teeth, said shield projecting vertically above the lower teeth, said shield, lower teeth and adjoining cheek defining a pocket for retaining food as it is being chewed, and said shield restricting movement of food from said pocket into the oral cavity.

17. An appliance for inhibiting lateral movement of a lower jaw with respect to an upper jaw in an oral cavity, said appliance comprising, in combination:
   a frame member;
   a wing member mounted on said frame member, said wing member having first and second oppositely positioned faces, said first face being disposed for facing relatonship with selected teeth within the oral cavity, and said second face being disposed for facing relationship with a person's tongue within the oral cavity;
   said wing member having first and second openings communicating between the first and second faces for receiving opposite ends of a wire to enable the appliance to be secured in a predetermined position within the oral cavity by wrapping the ends of the wire around a selected tooth; and,
   means for mounting said frame member onto a selected lower tooth or upper tooth with the appliance being held within the oral cavity in a predetermined position between the selected tooth and tongue, said wing member being vertically disposed between a first facing position adjacent a bottom tooth and a second facing position adjacent a top tooth, whereby lateral movement of the lower jaw is opposed by engagement of one of the upper or lower teeth against said wing member when the appliance is so mounted within the oral cavity.

* * * * *